US005552556A

United States Patent [19]

Miracle et al.

[11] Patent Number: 5,552,556

[45] Date of Patent: Sep. 3, 1996

[54] PERHYDROLYSIS-SELECTIVE BLEACH ACTIVATORS

[75] Inventors: Gregory S. Miracle, Forest Park; Alan D. Willey; Kevin L. Kott, both of Cincinnati; Michael E. Burns, West Chester, all of Ohio

[73] Assignee: The Procter & Gamble Company, Cincinnati, Ohio

[21] Appl. No.: 486,879

[22] Filed: Jun. 7, 1995

Related U.S. Application Data

[62] Division of Ser. No. 298,906, Aug. 31, 1994.

[51] Int. Cl.[6] ........................ C07D 233/20; A61K 31/41

[52] U.S. Cl. ................................. 548/334.1; 252/186.27; 252/186.3; 252/186.38; 252/186.39; 510/312

[58] Field of Search ............................... 252/94, 99, 102, 252/186.27, 186.3, 186.38, 186.39, 524, 542; 548/334.1

[56] References Cited

U.S. PATENT DOCUMENTS

| | | | |
|---|---|---|---|
| 2,647,135 | 7/1953 | Gunderson | 260/309.6 |
| 2,785,126 | 3/1957 | Scott et al. | 252/8.55 |
| 3,719,613 | 3/1973 | Marumo et al. | 252/542 |
| 3,951,878 | 4/1976 | Wakeman et al. | 252/542 |
| 3,988,433 | 10/1976 | Benedict | 424/53 |
| 4,058,488 | 11/1977 | Wakeman et al. | 252/542 |
| 4,199,464 | 4/1980 | Cambre | 252/91 |
| 4,238,497 | 12/1980 | Black et al. | 424/273 R |
| 4,260,529 | 4/1981 | Letton | 252/547 |
| 4,397,757 | 8/1983 | Bright et al. | 252/186.41 |
| 4,444,674 | 4/1984 | Gray | 252/95 |
| 4,539,130 | 9/1985 | Thompson et al. | 252/94 |
| 4,751,015 | 6/1988 | Humphreys et al. | 252/99 |
| 4,770,815 | 9/1988 | Baker et al. | 252/542 |
| 4,818,426 | 4/1989 | Humphreys et al. | 252/99 |
| 4,904,406 | 2/1990 | Darwent et al. | 252/102 |
| 4,933,103 | 6/1990 | Aoyagi et al. | 252/186.38 |
| 4,968,443 | 11/1990 | Lambert et al. | 252/8.8 |
| 4,988,451 | 1/1991 | Nunn et al. | 252/95 |
| 5,059,344 | 10/1991 | Aoyagi et al. | 252/186.38 |
| 5,093,022 | 3/1992 | Sotoya et al. | 252/102 |
| 5,106,528 | 4/1992 | Francis et al. | 252/186.23 |
| 5,143,641 | 9/1992 | Nunn | 252/186.38 |
| 5,245,075 | 9/1993 | Venturello et al. | 560/302 |
| 5,269,962 | 12/1993 | Brodbeck et al. | 252/186.25 |
| 5,294,362 | 3/1994 | Venturello et al. | 252/102 |

FOREIGN PATENT DOCUMENTS

| | | | |
|---|---|---|---|
| 508535 | 12/1954 | Canada . | |
| 284292 | 3/1988 | European Pat. Off. | 3/39 |
| 458396A1 | 5/1991 | European Pat. Off. | 3/39 |
| 475512A1 | 9/1991 | European Pat. Off. | 219/4 |
| 2756639 | 6/1978 | Germany . | |
| 2-115154 | 10/1988 | Japan | C07C 237/52 |
| 1311765 | 3/1973 | United Kingdom . | |
| 1382594 | 2/1975 | United Kingdom . | |
| WO94/01399 | 1/1994 | WIPO | 409/40 |
| WO94/02597 | 2/1994 | WIPO | C12N 9/28 |
| WO94/07944 | 4/1994 | WIPO | C08K 3/00 |

OTHER PUBLICATIONS

U.S. application ser. No. 08/249,581 Rai et al., May 24, 1995.

U.S. application ser. No. 08/298,650 Gosselink et al., Aug. 31 1994.

U.S. application ser. No. 08/298,903 Willey et al., Aug. 31, 1994.

U.S. application ser. No. 08/298,904 Taylor et al., Aug. 31, 1994.

*Primary Examiner*—Paul Lieberman

*Assistant Examiner*—Gregory R. Delcotto

*Attorney, Agent, or Firm*—Michael D. Jones; Brian M. Bolam; Kim William Zerby

[57] ABSTRACT

Bleaching compositions, laundry and automatic dishwashing detergent compositions comprising particular neutral or anionically charged substituted bleach activators are provided. More specifically, the invention relates to compositions which provide enhanced cleaning/bleaching benefits through the selection of perhydrolysis-selective bleach activators having specific leaving groups with a conjugate acid $pK_a$ above 13 and with specific ratios of the rate of perhydrolysis to the rate of hydrolysis and the rate of perhydrolysis to the rate of diacylperoxide production. Included are preferred activator compounds and methods for washing fabrics, hard surfaces, and tableware using the activators.

5 Claims, No Drawings

PERHYDROLYSIS-SELECTIVE BLEACH ACTIVATORS

This is a division of application Ser. No. 08/298,906, filed on Aug. 31, 1994.

FIELD OF THE INVENTION

The present invention relates to bleaching compositions comprising perhydrolysis-selective bleach activator compounds, especially certain types comprising cyclic amidine leaving groups, which are used to boost the performance of bleaching agents such as perborate and percarbonate. These perhydrolysis-selective bleach activators are suitable for use in fabric laundry and bleaching compositions, automatic dishwashing compositions, hard surface cleaners, and the like.

BACKGROUND OF THE INVENTION

The formulation of effective detergent compositions which are sufficiently robust to remove a wide variety of soils and stains from fabrics under a variety of usage conditions remains a considerable challenge to the laundry detergent industry. At least equal challenges are faced by the formulator of automatic dishwashing detergent compositions (ADD's), which are expected to efficiently cleanse and sanitize dishware, often under heavy soil loads. The problems associated with the formulation of truly effective cleaning compositions have been exacerbated by legislation which limits the use of effective phosphate builders in many regions of the world.

Most conventional cleaning compositions contain mixtures of various detersive suffactants to remove a wide variety of soils and stains from surfaces. In addition, various detersive enzymes, soil suspending agents, non-phosphorus builders, optical brighteners, and the like may be added in order to boost overall cleaning performance. Many fully-formulated cleaning compositions additionally contain bleach, which typically comprises a perborate or percarbonate compound. While quite effective at high temperatures, perborates and percarbonates lose much of their bleaching function at the low to moderate temperature ranges increasingly favored in consumer product applications. Accordingly, various bleach activators such as tetraacetylethylenediamine (TAED) and nonanoyloxy-benzenesulfonate (NOBS) have been developed to potentlate the bleaching action of perborate and percarbonate across a wide temperature range. NOBS is particularly effective on "dingy" fabrics.

Despite the usage of TAED and NOBS with bleaches in various cleaning and bleaching compositions, the search continues for still more effective activator materials, especially for those which do not form diacylperoxide byproducts. In general, perhydrolysis-selective activator materials should be safe, effective, and will preferably be designed to interact with troublesome soils and stains. Recently described new bleach activators include various cationically charged activators as well as non-charged types. The majority of activators in the literature have a conjugate acid aqueous $pK_a$ value of the leaving-group which is below 13. It is generally accepted that such bleach activators perhydrolyze at a desirable rate.

It has now been determined that certain selected bleach activators are effective in removing soils and stains from fabrics and hard surfaces. These activators are unexpectedly effective despite having a leaving-group conjugate acid aqueous $pK_a$ of greater than 13. Additionally, the activators of this invention have very advantageous high ratios of rates of perhydrolysis to hydrolysis and of perhydrolysis to diacylperoxide formation. Without being limited by theory, these unusual rate ratios lead to a number of significant benefits for the bleach activators of the invention, including increased efficiency, avoidance of wasteful byproduct formation in the wash, increased color compatibility, increased enzyme compatibility, and better stability on storage.

By the present invention, commercially attractive bleach activators are provided, for example through the use of 4,5-dihydroimidazole-based chemistry. The bleach activators herein are effective for removing soils and stains not only from fabrics, but also from dishware in automatic dishwashing compositions. The activators are designed to function well over a wide range of washing or soaking temperatures. The activators herein are safe on rubber surfaces, such as the rubber sump hoses which are often used in some European front loading washing machines. Thus, the bleach activators herein provide a substantial advance over activators known in the art, as will be seen from the disclosures hereinafter.

BACKGROUND ART

Bleach activators are well known in the literature. See, for example, the section "Conventional Bleach Activators" hereinafter.

SUMMARY OF THE INVENTION

The present invention encompasses bleach activator compositions comprising:

(a) an effective amount of a source of hydrogen peroxide; and (b) an effective amount of a neutral or anionically charged bleach activator selected from:

(i) $Z(C(X)L)_x$ wherein x is 1 or 2 or 3, preferably x is 1 or 2;

(ii) $L'(C(X)Z)_y$ wherein y>2, preferably from about 2 to about 4, more preferably about 2; and (iii) mixtures thereof;

provided that:

when said bleach activator is anionically charged, said bleach activator further comprises a charge-balancing number of compatible counter-cations; L and L' are leaving-groups comprising at least one tri-coordinate nitrogen atom wherein LH and $L'H_y$, the conjugate acids of L and L', are non-charged or anionically charged; at least one L in (i) is a non-lactam leaving group, for example a 4,5-dihydroimidazole as further disclosed hereinafter; a tri-coordinate nitrogen atom in each L or L' covalently connects said L or L' to a moiety —C(X)— forming a group LC(X)— or L' C(X)— for example as in:

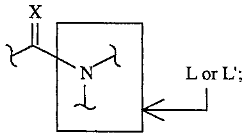

L or L';

when x> 1, the L in (i) are the same or different, preferably the same, the —C(X)Z in (ii) are the same or different, preferably the same; the aqueous $pK_a$ of the conjugate acid of at least one L or L', preferably all L or L', with respect to its —C(X)— connected tri-coordinate nitrogen atom is about 13 or greater; Z is a non-charged or anionically charged moiety comprising at least two carbon atoms, each Z being covalently connected to at least one moiety —C(X)—; any atom in Z to which any —C(X)L or —C(X)L' is directly bonded is a carbon atom; and X is selected from the group consisting of =0, =N— and =S, preferably =0; and further provided that said bleach activator has a ratio of:

(i) $kp/k_H > 4$, preferably $kp/k_H > 10$, more preferably $kp/k_H > 50$, most preferably $kp/k_H > 500$, wherein kp is the rate constant for perhydrolysis of said bleach activator and $k_H$ is the rate constant for hydrolysis of said bleach activator; and said bleach activator has a ratio of:

(ii) $kp/k_D > 5$, preferably $kp/k_D > 10$, more preferably $kp/k_D > 50$, wherein kp is as defined in (i) and wherein $k_D$ is the rate constant for formation of a diaeylperoxide from said bleach activator.

In general, said bleach activator has $k_H$ no greater than about 10 $M^{-1}$ $s^{-1}$, preferably no greater than about 5 $M^{-1}$ $s^{-1}$.

Preferred bleaching compositions of this invention comprise leaving-groups with a conjugate acid $pK_a$ of no more than about 33, more preferably no more than about 28, as measured in DMSO solvent. Moreover, preferred bleach activators have a perhydrolysis efficiency, as defined hereinafter, of at least 10%, preferably at least 20%.

Bleaching systems of this invention typically comprise at least about 0.1%, preferably from about 0.1% to about 50%, by weight, of the perhydrolysis-selective bleach activators as defined herein, and at least about 0.1%, preferably from about 0.1% to about 50%, by weight, of a source of hydrogen peroxide. Optionally but preferably, the bleaching system further comprises at least 0.1%, preferably from about 0.1% to about 10% of a chelant.

The invention also encompasses automatic dishwashing detergents, hard surface cleaners, and laundry detergent compositions. Thus, the bleaching composition of this invention may further comprise a member selected from the group consisting of:

a laundry detergent surfactant, preferably selected from the group consisting of ethoxylated surfactants, sugar-derived surfactants, sarcosinates and amine oxides;

a low-foaming automatic dishwashing surfactant; and a bleach-stable thickener.

Optionally but preferably, the bleaching compositions further comprise at least one anionic surfactant such that an aqueous solution comprising the anionic surfactant and a bleach activator of this invention forms no visible precipitate at ambient temperature.

An example of a preferred granular laundry detergent comprises:

a) from about 0.1% to about 10% of a bleach activator according to this invention;

b) from about 0.5% to about 25% of a source of hydrogen peroxide in the form of a perborate or percarbonate salt; and c) from about 0.5% to about 25% of a detersive surfactant.

An example of a granular automatic dishwashing detergent comprises:

a) from about 0.1% to about 10% of a bleach activator according to this invention;

b) from about 0.5% to about 25% of a source of hydrogen peroxide in the form of a perborate or percarbonate salt; and c) from about 0.1% to about 7% of a low-foaming surfactant.

The compositions of this invention may optionally comprise detergent builder and conventional bleach activators as described hereinafter. Highly preferred conventional bleach activators are selected from the group consisting of alkanoyloxybenzenesulfonates, tetraacetylethylenediamine, and mixtures thereof. The bleaching composition of this invention may further comprise transition-metal containing bleach catalysts, as further illustrated in detail hereinafter. Optional but preferred builders useful herein are selected from the group consisting of citrate, layered silicate, zeolite A, zeolite P and mixtures thereof.

The invention also encompasses a method for removing stains from fabrics or hard surfaces, especially dishware, comprising contacting said stains with a source of hydrogen peroxide and a neutral or anionically charged bleach activator compound in the presence of water, preferably with agitation. Typically the activator will be present at levels of at least about 20 ppm in the water. The hydrogen peroxide source will typically be present at levels of at least 50 ppm.

By "effective amount" herein is meant an amount which is sufficient, under whatever comparative test conditions are employed, to enhance cleaning of a soiled surface. Likewise, the term "catalytically effective amount" refers to an amount which is sufficient under whatever comparative test conditions are employed, to enhance cleaning of a soiled surface.

All percentages, ratios and proportions herein are by weight, unless otherwise specified. All documents cited are, in relevant part, incorporated herein by reference.

DETAILED DESCRIPTION OF THE INVENTION

A highly preferred bleach activator of this invention has the formula:

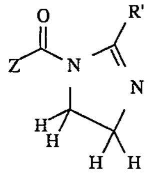

wherein Z is selected from the group consisting of $C_2$–$C_{16}$ linear or branched, saturated or unsaturated, unsubstituted or substituted (for example, ethoxylated) alkyl, alkaryl, aralkyl and aryl; and R' is selected from the group consisting of: H, $C_{1-C5}$ alkyl, ethoxylated alkyl, carboxylated alkyl, sulfated alkyl, sulfonated alkyl, phenyl, substituted phenyl, and mixtures thereof. More preferably, Z is selected from the group consisting of phenyl, nitrophenyl, chlorophenyl, t-butylphenyl, and $C_{8-12}$ linear or branched, saturated or unsaturated alkyl; and R' is H or methyl.

In another preferred embodiment R' is selected from the group consisting of carboxylated alkyl, sulfated alkyl and sulfonated alkyl, wherein the anionic charge of R' is balanced by a cation selected from the group consisting of $H^+$, $Na^+$ , $K^+$ , and $C_{1-C4}$ quaternary ammonium.

The bleach activators of the invention can be made by conventional synthesis techniques, as will be apparent from the illustration hereinafter. For example, commercially available mono-, di- or tricarboxylic acids are readily convened to acid chlorides from which compounds such as those having preferred formula (i) are readily made.

Moieties Z—Moieties Z herein can be those named in connection with the above preferred embodiment. Further illustrations of suitable Z are the following:

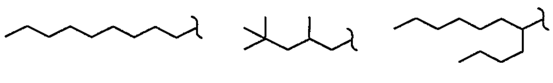

-continued

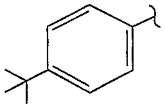

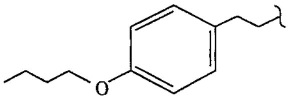

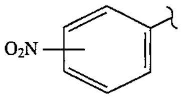

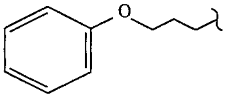

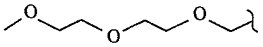

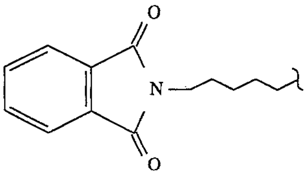

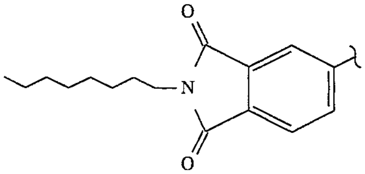

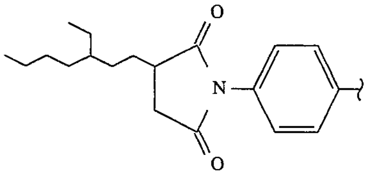

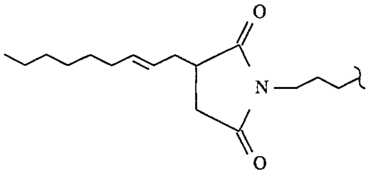

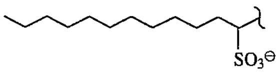

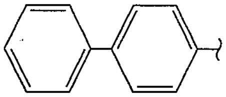

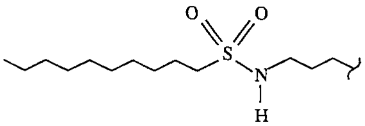

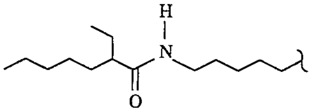

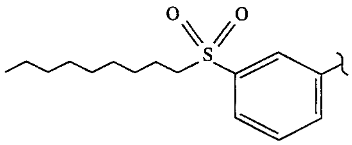

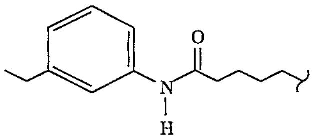

-continued

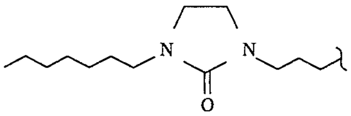

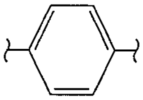

In yet another preferred embodiment, the bleach activator has the formula:

L—C(O)—(Z)$_i$—C(O)—L wherein the two moieties L can be selected independently, i is 0 or 1 and Z is selected from the group consisting of $C_{2-16}$ alkyl, $C_{2-16}$ alkaryl, $C_{2-16}$ aralkyl, $C_{2-16}$ aryl, and mixtures thereof. Any of the members of the foregoing group can be linear, cyclic or branched, saturated or unsaturated, substituted or unsubstituted. Preferably Z is p- $C_6H_4$.

In general, the bleach activators of this invention can be in the form of an acid salt.

Leaving-group, L—The leaving-group(s) L, in the substituted bleach activators herein are generally selected so as to respect the above-summarized requirements.

Preferred L are selected from the group consisting of cyclic amidines with a ring size of from about 5 to about 12 atoms:

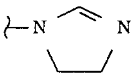

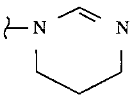

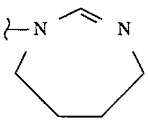

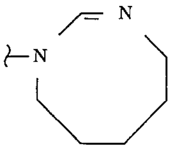

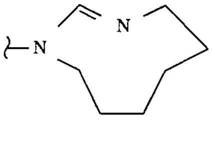

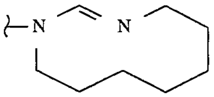

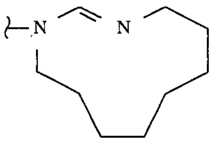

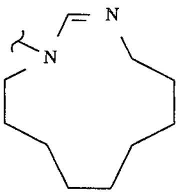

Preferred cyclic amidines have a ring size of from about 5 to about 7 atoms as in the first three of the above structures.

At least in part, the moieties L can be selected from the group consisting of lactams with a ring size of from about 6 to about 12:

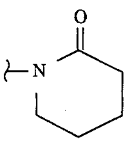

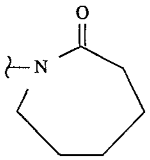

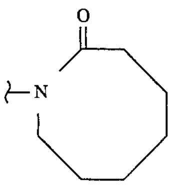

-continued

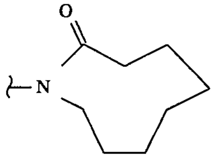

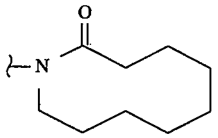

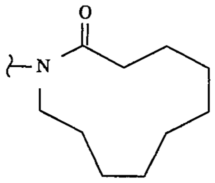

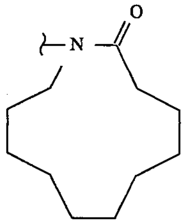

Preferred lactam ring sizes are of from about 6 to about 7 atoms as in the first two of the above structures.

Also, anilino derivatives are within the scope of allowable leaving-groups L herein. Such anilino derivatives are further illustrated as follows:

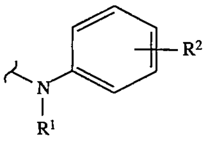

which includes compounds wherein $R^1$ and $R^2$ may be fused, e.g.,

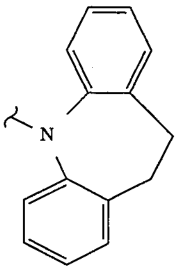

Mixtures of leaving-groups are possible within the same substituted bleach activator structure, for example, as in:

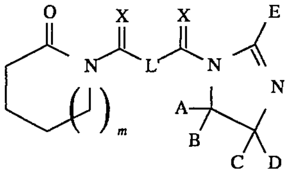

wherein m is 1 or 2 and A, B, C, and D are each selected independently (including cases in which two or more cyclic amidines are present in the same bleach activator molecule) and are as defined hereinafter. Moreover, leaving-groups L' herein can also include types such as the following:

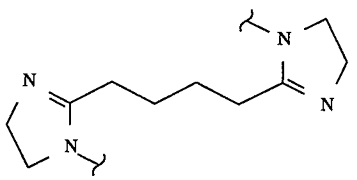

-continued

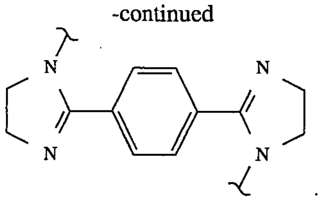

.

Alternative L' moieties are readily synthesized from a variety of dicarboxylic or tricarboxylic acids, from which amidine derivatives, such as those illustrated, are obtainable by dehydration. Mixtures of any of the perhydrolysis-selective bleach activators with each other or with conventional bleach activators are quite acceptable for use in the instant bleaching compositions.

Recalling that bleach activators according to the invention can have the formula (i) $Z(C(X)L)_x$ wherein x is 1 or 2 or 3, preferably x is 1 or 2, in a preferred embodiment of formula (i), L is the 4,5-saturated 5-membered cyclic amidine having the formula:

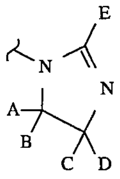

wherein A, B, C, D and E are selected from the group consisting of H, alkyl, aryl, substituted alkyl, substituted aryl, and substituted alkaryl. In a particularly preferred example of this embodiment, when E is an alkyl group of greater than 5 carbon atoms in length, no more than three of A, B, C and D are H. In still another preferred example of this embodiment, E is selected from H and $C_1$–$C_5$ alkyl and A, B, C, and D are all H.

Note, the peracid produced on reacting bleach activators comprising such leaving-groups with hydrogen peroxide is different from peracetic acid.

Moieties X—As noted hereinabove, X in the perhydrolysis-selective bleach activators can be =O, =S, or =N–. When X is =O or =S, it is immediately apparent what structures are encompassed. When X is =N—, the following structures further illustrate the perhydrolysis-selective bleach activators encompassed herein:

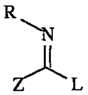

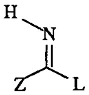

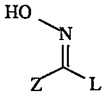

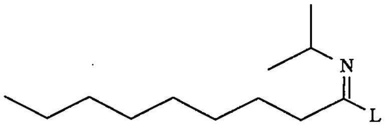

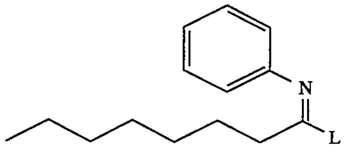

-continued

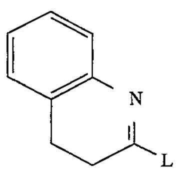

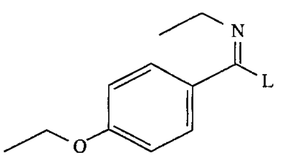

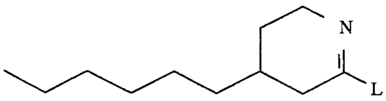

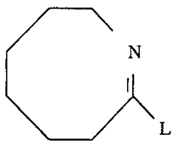

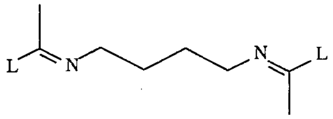

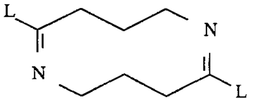

It is understood that

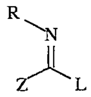

is generally equivalent to

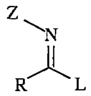

as further illustrated in the following embodiments:

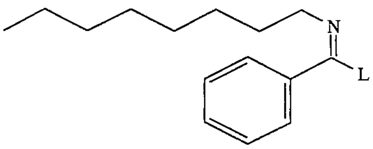

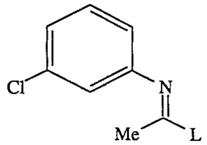

Counter-ions—The perhydrolysis-selective bleach activators herein may, optionally, comprise counter-ions, for example when one or more anionic substituents are present in the molecule. Suitable counter-ions herein include sodium, potassium and $C_1$–$C_5$ quaternary ammonium.

Electron-withdrawing substitutents—In one preferred mode, bleaching compositions herein preferably comprise the perhydrolysis-selective bleach activators comprising at least one electron-withdrawing or aromatic substituent in Z, such that the $pK_a$ of the peracid formed by the activator, e.g., ZC(O)OOH is less than the $pK_a$ of the nonsubstituted form. Preferably the electron-withdrawing substituent is neutral. More preferably the electron-withdrawing substituent is nitro, an aromatic moiety having an electron-withdrawing effect, or a combination of the two.

The effects of electron withdrawing substituents on the aqueous $pK_a$ of aliphatic and aromatic peroxy acids are well understood and documented (see W. M. Richardson, in *The Chemistry of the Functional Groups, Peroxides,* Ed. S. Patai, Wiley, N.Y., 1983, Chapter 5, pp 130, 131 and references therein). Without being limited by theory, it is believed that stronger peracids provide enhanced performance.

Surface Activity—For laundry detergent compositions and bleaching compositions, preferably the perhydrolysis-selective bleach activator is surface-active, having a critical micelie concentration of less than or equal to about $10^{-2}$ molar. Such surface-active activators preferably comprise, in total, exactly one long-chain moiety having a chain of from about 8 to about 12 atoms; counter-ions, if present (for example as in an anionically substituted perhydrolysis-selective bleach activator) is preferably non surface-active. The term "surface active" is well-known in the art and characterizes compounds which comprise at least one group with an affinity for the aqueous phase and a group, typically a hydrocarbon chain, which has little affinity for water. Surface active compounds dissolved in a liquid, in particular in water, lower the surface tension or interfacial tension by positive adsorption at the liquid/vapor interface, or the soil-water interface. Critical micelie concentration ($c_m$ or "cmc"): is likewise a recognized term, referring to the characteristic concentration of a surface active agent in solution above which the appearance and development of micelies brings about sudden variation in the relation between the concentration and certain physico-chemical properties of the solution. Said physico-chemical properties include density, electrical conductivity, surface tension, osmotic pressure, equivalent electrical conductivity and interfacial tension. Whereas high surface activity and low cmc is preferred in some applications of MSBA's, in other applications, such as cleaning of certain hydrophilic soils, low surface activity and high cmc, e.g., about $10^{-1}$ molar or higher, may be desirable. Thus, in view of the range of applications contemplated, a wide range of cmc and surface activity for MSBA's is within the spirit and scope of the present invention.

$pK_a$, Rate and Perhydrolysis Criticalities

In accordance with the present invention, there are provided bleaching compositions wherein the perhydrolysis-selective bleach activators respect criticalities of $pK_a$ and criticalities relating to rates of perhydrolysis, hydrolysis and diacylperoxide formation. Furthermore, perhydrolysis efficiency is important in selecting the bleach activator. All of these criticalities will be better understood and appreciated in light of the following disclosure.

$pK_a$ Value—The acids in which organic chemists have traditionally been interested span a range, from the weakest acids to the strongest, of about 60 pK units. Because no single solvent is suitable over such a wide range, establishment of comprehensive scales of acidity necessitates the use of several different solvents. Ideally, one might hope to construct a universal acidity scale by relating results obtained in different solvent systems to each other. Primarily because solute-solvent interactions affect acid-base equilibria differently in different solvents, it has not proven possible to establish such a scale.

Water is taken as the standard solvent for establishing an acidity scale. It is convenient, has a high dielectric constant, and is effective at solvating ions. Equilibrium acidities of a host of compounds (e.g., carboxylic acids and phenols) have been determined in water. Compilations of pK data may be found in Perrin, D. D. "Dissociation Constants of Organic Bases in Aqueous Solution"; Butterworths: London, 1965 and Supplement, 1973; Serjeant, E. P.; Dempsey, B. "Ionisation Constants of Organic Acids in Aqueous Solution"; 2nd ed., Pergammon Press: Oxford, 1979. Experimental methods for determining $pK_a$ values are described in the original papers. The $pK_a$ values that fall between 2 and 10 can be used with a great deal of confidence; however, the further removed values are from this range, the greater the degree of skepticism with which they must be viewed.

For acids too strong to be investigated in water solution, more acidic media such as acetic acid or mixtures of water with perchloric or sulfuric acid are commonly employed; for acids too weak to be examined in water, solvents such as liquid ammonia, cyclohexylamine and dimethylsulfoxide have been used. The Hammett $H_o$ acidity function has allowed the aqueous acidity scale, which has a practical $pK_a$ range of about 0–12, to be extended into the region of negative $pK_a$ values by about the same range. The use of $H\_$ acidity functions that employ strong bases and cosolvents has similarly extended the range upward by about 12 $pK_a$ units.

The present invention involves the use of leaving groups the conjugate acids of which are considered to be weak; they possess aqueous $pK_a$ values greater than about 13. To establish only that a given compound has an aqueous $pK_a$ above about 13 is straightforward. As noted above, values much above this are difficult to measure with confidence without resorting to the use of an acidity function. While the measurement of the acidity of weak acids using the $H\_$ method has the advantage of an aqueous standard state, it is restricted in that (1) it requires extrapolation across varying solvent media and (2) errors made in determining indicator $pK_a$ values are cumulative. For these and other reasons, Bordwell and co-workers have developed a scale of acidity in dimethylsulfoxide (DMSO), and it is this scale which we use to define the upper limits of $pK_a$ for the conjugate acids of our leaving groups. This solvent has the advantage of a relatively high dielectric constant ($\epsilon$= 47); ions are therefore dissociated so that problems of differential ion pairing are reduced. Although the results are referred to a standard state in DMSO instead of in water, a link with the aqueous $pK_a$ scale has been made. When acidities measured in water or on a water-based scale are compared with those measured in DMSO, acids whose conjugate bases have their charge localized are stronger acids in water; acids whose conjugate bases have their charge delocalized over a large area are usually of comparable strength. Bordwell details his findings in a 1988 article (*Acc. Chem. Res.* 1988, 21, 456–463). Procedures for measurement of $pK_a$ in DMSO are found in papers referenced therein.

Definitions of $k_H$, $k_P$ and $k_D$—In the expressions given below, the choice of whether to use the concentration of a nucleophile or of its anion in the rate equation was made as a matter of convenience. One skilled in the art will realize that measurement of solution pH provides a convenient means of directly measuring the concentration of hydroxide ions present. One skilled in the art will further recognize that use of the total concentrations of hydrogen peroxide and peracid provide the most convenient means to determine the rate constants $k_P$ and $k_D$.

The terms, such as RC(O)L, used in the following definitions and in the conditions for the determination of $k_H$, $k_P$ and $k_D$, are illustrative of a general bleach activator structure and are not limiting to any specific bleach activator herein. Thus, the term "RC(O)L" could be substituted with "ZC(X)L", etc.

Definition of $k_H$ $$RC(O)L+HO^{-} \rightarrow RC(O)O^{-} + HL$$

The rate of the reaction shown above is given by $$Rate=k_H[RC(O)L][HO^-]$$

The rate constant for hydrolysis of bleach activator ($k_H$) is the second order rate constant for the bimolecular reaction between bleach activator and hydroxide anion as determined under the conditions specified below.

Definition of $k_P$ $$RC(O)L+H_2O_2 \rightarrow RC(O)O_2H+ HL$$

The rate of the reaction shown above is given by $$Rate=k_P[RC(O)L][H_2O_2]_T$$

where $[H_2O_2]_T$ represents the total concentration of hydrogen peroxide and is equal to $[H_2O_2]+[HO_2^-]$.

The rate constant for perhydrolysis of bleach activator ($k_P$) is the second order rate constant for the bimolecular reaction between bleach activator and hydrogen peroxide as determined under the conditions specified below.

Definition of $k_D$ $$RC(O)L+RC(O)O_2H \rightarrow RC(O)O_2C(O)R+ HL$$

The rate of the reaction shown above is given by $$Rate= k_D'[RC(O)L][RC(O)O_2H]_T$$

where $[RC(O)O_2H]_T$ represents the total concentration of peracid and is equal to $[RC(O)O_2H_1+[RC(O)O_2^-]$.

The rate constant for the formation of a diacylperoxide from the bleach activator ($k_D$), the second order rate constant for the bimolecular reaction between bleach activator and peracid anion, is calculated from the above defined $k_{D'}$. The value for $k_{D'}$, is determined under the conditions specified below.

Conditions for the Determination of Rate Constants

Hydrolysis—A set of experiments is completed to measure the rate of hydrolysis of a bleach activator RC(O)L in aqueous solution at total ionic strength of 1M as adjusted by addition of NaCl. The temperature is maintained at 35.0±0.1° C. and the solution is buffered with $NaHCO_3$+ $Na_2CO_3$. A solution of the activator ([RC(O)L]=0.5 mM) is reacted with varying concentrations of NaOH under stopped-flow conditions and the rate of reaction is monitored optically. Reactions are run under pseudo first-order conditions to determine the bimolecular rate constant for hydrolysis of bleach activator ($k_H$). Each kinetic run is repeated at least five times with about eight different concentrations of hydroxide anions. All kinetic traces give satisfactory fits to a first-order kinetic rate law and a plot of the observed first-order rate constant versus concentration of hydroxide anion is linear over the region investigated. The slope of this line is the derived second order rate constant $k_H$.

Perhydrolysis— A set of experiments is completed to measure the rate of perhydrolysis of a bleach activator RC(O)L in aqueous solution at pH=10.0 with constant ionic strength of 1M as adjusted by addition of NaCl. The temperature is maintained at 35.0±0.1° C. and the solution is buffered with $NaHCO_3$+$Na_2CO_3$. A solution of the activator ([RC(O)L]=0.5 mM) is reacted with varying concentrations of sodium perborate under stopped-flow conditions and the rate of reaction is monitored optically. Reactions are run under pseudo first-order conditions in order to determine the bimolecular rate constant for perhydrolysis of bleach activator ($k_P$). Each kinetic run is repeated at least five times with about eight different concentrations of sodium perborate. All kinetic traces give satisfactory fits to a first-order kinetic rate law and a plot of the observed first-order rate constant versus total concentration of hydrogen peroxide is linear over the region investigated. The slope of this line is the derived second order rate constant $k_P$. One skilled in the an recognizes that this rate constant is distinct from, but related to, the second order rate constant for the reaction of a bleach activator with the anion of hydrogen peroxide ($k^{mic}$). The relationship of these rate constants is given by the following equation:

$$k_{mic}=k_P\{(K_a+[H^+])/K_a\}$$

where $K_a$ is the acid dissociation constant for hydrogen peroxide.

Formation of diacylperoxide—A set of experiments is completed to measure the rate of formation of a diacylperoxide $RC(O)O_2C(O)R$ from a bleach activator RC(O)L in aqueous solution at pH= 10.0 with constant ionic strength of 1M as adjusted by addition of NaCl. The temperature is maintained at 35.0+0.1° C. and the solution is buffered with $NaHCO_3$+ $Na_2CO_3$. A solution of the activator ([RC(O)L]= 0.5 mM) is reacted with varying concentrations of peracid under stopped-flow conditions and the rate of reaction is monitored optically. Reactions are run under pseudo first-order conditions in order to determine the bimolecular rate constant $k_{D'}$. Each kinetic run is repeated at least five times with about eight different concentrations of peracid anion. All kinetic traces give satisfactory fits to a first-order kinetic rate law and a plot of the observed first-order rate constant versus total concentration of peracid is linear over the region investigated. The slope of this line is the derived second order rate constant $k_{D'}$. The bimolecular rate constant for the formation of a diacylperoxide from peracid anion ($k_D$) is calculated according to $$k_D= k_{D'}\{(K_a+[H^+])/K_a\}$$

where $K_a$ is the acid dissociation constant for the peracid $RC(O)O_2H$. One skilled in the art will realize that the $pK_a$ values for peracids fall into a rather narrow range from about 7 to about 8.5 and that at pH=10.0, when $K_a$> about $10^{-8}$, $\{(K_a+[H^+])/K_a\}\cong 1$ and $k_D\}k_{D'}$.

Test for Perhydrolysis Efficiency—This method is applicable as a test for screening any bleach activators RC(O)L (not intending to be limiting of any specific perhydrolysis-selective bleach activator structure herein) by confirmation of the formation of peracid analyte $RC(O)O_2H$. The minimum standard for perhydrolysis efficiency (PE) is the generation of >10% of theoretical peracid within 10 minutes when tested under the conditions specified below.

Test Conditions—Distilled, deionized water at 40° C. adjusted to pH=10.3 with $Na_2CO_3$, 100 ppm bleach activator RC(O)L, 500 ppm sodium percarbonate Test Protocol—Distilled, aleionized water (90 mL; pH adjusted to 10.3 with $Na_2CO_3$) is added to a 150 mL beaker and heated to 40°±1° C. Fifty (50) mg sodium percarbonate is added to the beaker and the mixture is stirred two minutes before a 10 mL solution containing 10 mg of bleach activator (predissolved in 1 mL of a water miscible organic solvent (e.g., methanol or dimethylformamide) and brought to volume with pH 10.3 distilled, deionized water) is added. The initial time point is taken 1 minute thereafter. A second sample is removed at 10 minutes. Sample aliquots (2 mL) are examined via analytical HPLC for the quantitative determination of peracid $RC(O)O_2H$.

Sample aliquots are individually mixed with 2 mL of a pre-chilled 5° C. solution of acetonitfile/acetic acid (86/14) and placed in temperature controlled 5° C. autosampler for subsequent injection onto the HPLC column.

High performance liquid chromatography of the authentic peracid under a given set of conditions establishes the characteristic retention time ($^tR$) for the analyte. Conditions for the chromatography will vary depending on the peracid of interest and should be chosen so as to allow baseline separation of the peracid from other analytes. A standard calibration curve (peak area vs. concentration) is constructed using the peracid of interest. The analyte peak area of the 10 minute sample from the above described test is thereby converted to ppm peracid generated for determination of the quantity PE. A bleach activator is considered acceptable when a value of PE=[(ppm of peracid generated)/(theoretical ppm peracid)]×100% >10% is achieved within ten minutes under the specified test conditions.

To note, by comparison with 4,5-saturated cyclic amidine embodiments of the instant bleach activators, known closely related chemical compounds wherein the 4,5 position is unsaturated have surprisingly greater rates of hydrolysis. Specifically, acetyl imidazole has $k_H$ greater than 10.0 $M^{-1}$ $s^{-1}$: Accordingly this invention does not encompass imidazole as a leaving group.

Determination of $k_H$, $k_P$ and $k_D$ when Bleach Activator has formula $Z(C(X)L)_x$ wherein x>1; or has formula $L'(C(X)Z)_y$.

The present invention comprises bleach activator embodiments wherein there are single or multiple C(X)L groups. When only a single —C(X)L moiety is present, measurement of $k_H$, $k_P$ and $k_D$ is accomplished straightforwardly as described hereinabove. When the perhydrolysis-selective bleach activator comprises multiple —C(X)L or multiple —C(X)Z groups, those skilled in the art will realize that the determination of $k_H$, $k_P$ and $k_D$ for such bleach activators is best accomplished through the use of model compounds. "Model compounds" herein are chemical compounds identified purely for purposes of simplifying testing and measurement, and are not required to lie within the instant invention (though they may in certain instances do so). The formula of model compounds is generally arrived at by replacing all but one of the —C(X)L or —C(X)Z moieties in any multiple —C(X)L or multiple —C(X)Z -containing perhydrolysis-selective bleach activator with methyl or H.

A number of different cases are identified, depending on the precise formula of the perhydrolysis-selective bleach activator:

For bleach activators of formula $Z(C(X)L)_x$ wherein x>1:

Case (i)[a] When Z is symmetric and all C(X)L groups are identical, a single model compound is required.

Case (i)[b] When Z is symmetric and all C(X)L groups are not identical, x model compounds are needed.

Case (i)[c] When Z is asymmetric, x model compounds are needed regardless of whether or not all C(X)L groups are identical.

For bleach activators of formula $L'(C(X)Z)_y$:

Case (ii)[a] When L' is symmetric and all C(X)Z groups are identical, a single model compound is required.

Case (ii)[b] When L' is symmetric and all C(X)Z groups are not identical, y model compounds are needed.

Case (ii)[c] When L' is asymmetric, y model compounds are needed regardless of whether or not all C(X)Z groups are identical.

The choice of suitable model compounds is nonlimitingly illustrated as follows. Examples of each case described above are illustrated below.

Case (i)[a]

-continued
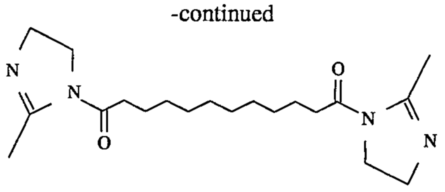
A model compound for the above is:
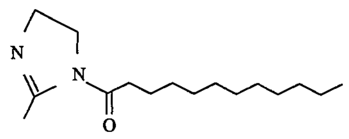
Case (i)[b]
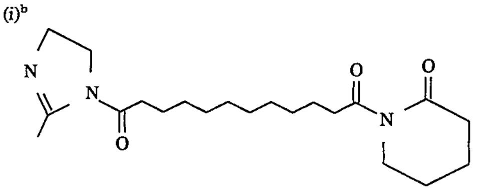
Model compounds for the above are:
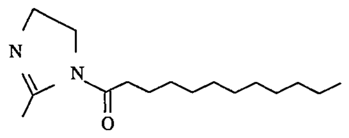
and
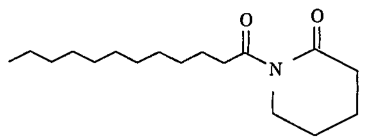
Case (i)[c]
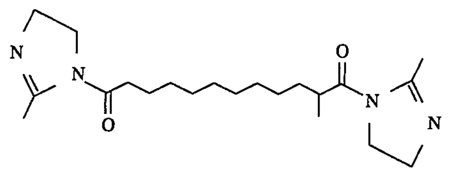
Model compounds for the above are:
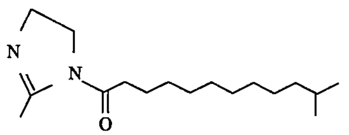
and
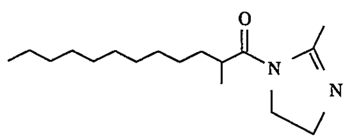
Case (ii)[a]
-continued
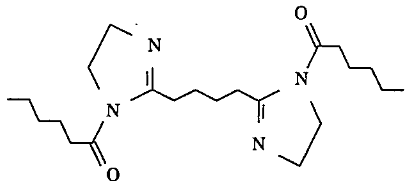
A model compound for the above is:
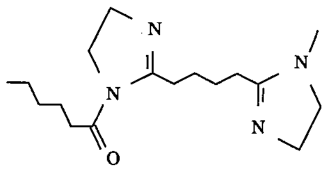
Case (ii)[b]
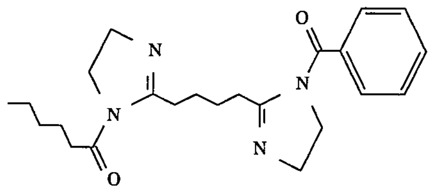
Model compounds for the above are:
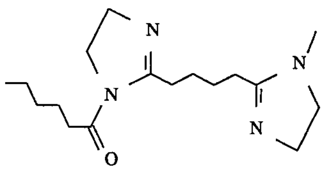
and
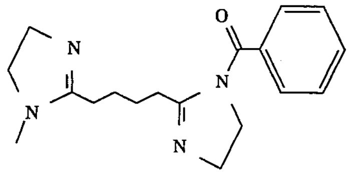
Case (ii)[c]
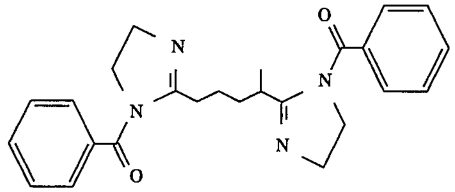
Model compounds for the above are:
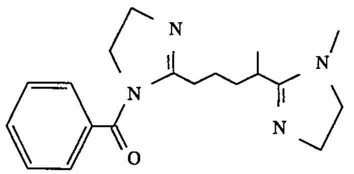
and -continued

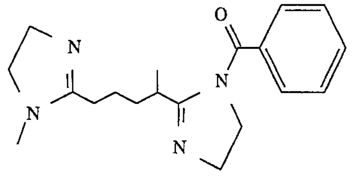

The above examples are given by way of illustration. One skilled in the art will realize that if the connection between any two —C(X)L (or —C(X)Z) is conjugated, any electronic effect of one —C(X)L (or —C(X)Z) on the kinetics of the other must be suitably accounted for in the model compounds chosen.

When model compounds have been selected for a multiple —C(X)L or multiple —C(X)Z -containing perhydrolysis-selective bleach activator, $k_H$, $k_P$ and $k_D$ are measured for each model compound as described hereinabove. The bleach activator corresponding to the set of model compounds is considered to conform with the $k_P/k_H$, $k_P/k_D$ and $k_H$ criticalities of the invention provided that: all model compounds meet the specified $k_P/k_D$ and $k_H$ criticalities; and at least one model compound meets the specified $k_P/k_H$ criticality.

Bleaching Compositions—The perhydrolysis-selective bleach activators herein are not preferably employed alone but in combination with a source of hydrogen peroxide, as disclosed hereinafter. Levels of the perhydrolysis-selective activators herein may vary widely, e.g., from about 0.05% to about 95%, by weight, of composition, although lower levels, e.g., from about 0.1% to about 20% are more typically used.

Source of hydrogen peroxide—A source of hydrogen peroxide herein is any convenient compound or mixture which under consumer use conditions provides an effective amount of hydrogen peroxide. Levels may vary widely and are typically from about 0.5% to about 60%, more typically from about 0.5% to about 25%, by weight of the bleaching compositions herein.

The source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Mixtures of any convenient hydrogen peroxide sources can also be used.

A preferred percarbonate comprises dry particles of sodium percarbonate having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

While effective bleaching compositions herein may comprise only the bleach activators of the invention and a source of hydrogen peroxide, fully-formulated laundry and automatic dishwashing compositions typically will further comprise adjunct ingredients to improve or modify performance. Typical, non-limiting examples of such ingredients are disclosed hereinafter for the convenience of the formulator.

Adjunct Ingredients

Bleach catalysts—If desired, the bleaches can be catalyzed by means of a manganese compound. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; and European Pat. App. Pub. Nos. 549,271A1, 549,272A1, 544,440A2, and 544,490A1; Preferred examples of these catalysts include: $Mn^{IV}_2(u\text{-}O)_3$(1,4,7-trimethyl-1,4,7-triazacyclononane)$_2(PF_6)_2$, $Mn^{III}_2(u\text{-}O)_1(u\text{-}OAc)_2$(1,4,7-trimethyl-1,4,7-triazacyclononane)$_2$ -$(ClO_4)_2$, $Mn^{IV}_4(u\text{-}O)_6$(1,4,7-triazacyclononane)$_4(ClO_4)_4$, $Mn^{III}$-$Mn^{IV}_4$-$(u\text{-}O)_1(u\text{-}OAc)_2$-(1,4,7-trimethyl-1,4,7 -triazacyclo-nonane)$_2(ClO_4)_3$, $Mn^{IV}$(1,4,7-trimethyl-1,4,7-triazacyclo-nonane)-$(OCH_3)_3(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Said manganese can be precomplexed with ethylenediaminedisuccinate or separately added, for example as a sulfate salt, with ethylenediaminedisuccinate. (See U.S. application Ser. No. 08/210,186, filed Mar. 17, 1994.) Other preferred transition metals in said transition-metal-containing bleach catalysts include iron or copper.

As a practical matter, and not by way of limitation, the bleaching compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 50 ppm, of the catalyst species in the laundry liquor.

Conventional Bleach Activators—"Conventional bleach activators" herein are any bleach activators which do not respect the above-identified provisions given in connection with the MSBAs. Numerous conventional bleach activators are known and are optionally included in the instant bleaching compositions. Various nonlimiting examples of such activators are disclosed in U.S. Pat. No. 4,915,854, issued Apr. 10, 1990 to Mao et al, and U.S. Pat. No. 4,412,934. The nonanoyioxybenzene sulfonate (NOBS) and tetraacetyl ethylenediamine (TAED) activators are typical, and mixtures thereof can also be used. See also U.S. Pat. No. 4,634,551 for other typical conventional bleach activators. Known amido-derived bleach activators are those of the formulae: $R^1N(R^5)C(O)R^2C(O)L$ or $R^1C(O)N(R^5)R^2C(O)L$ wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. Further illustration of optional, conventional bleach activators of the above formulae include (6 -octanamido-caproyl)oxybenzenesulfonate, (6-nonanamidocaproyl)oxybenzenesulfonate, (6-decanamido-caproyl)oxybenzenesulfonate, and mixtures thereof as described in U.S. Pat. No. 4,634,551. Another class of conventional bleach activators comprises the benzoxazin-type activators disclosed by Hodge et al in U.S. Pat. No. 4,966,723, issued Oct. 30, 1990. Still another class of conventional bleach activators includes those acyl lactam activators which do not contain any cationic moiety, such as acyl caprolactams and acyl valerolactams of the formulae $R^6C(O)L^1$ and $R^6C(O)L^2$ wherein $R^6$ is H, an alkyl, aryl, alkoxyaryl, or alkaryl group containing from 1 to about 12 carbon atoms, or a substituted phenyl group containing from about 6 to about 18 carbons and wherein $L^1$ and $L^2$ are caprolactam or valerolactam moieties. See copending U.S. applications Ser. No. 08/064, 562 and 08/082,270, which disclose substituted benzoyl lactams. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, which discloses acyl caprolactams, including benzoyl caprolactam, adsorbed into sodium perborate.

Bleaching agents other than hydrogen peroxide sources are also known in the art and can be utilized herein as adjunct ingredients. One type of non-oxygen bleaching gent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonated zinc phthalocyanine.

Organic Peroxides, especially Diacyl Peroxides—are extensively illustrated in Kirk Othmer, Encyclopedia of Chemical Technology, Vol. 17, John Wiley and Sons, 1982 at pages 27–90 and especially at pages 63–72, all incorporated herein by reference. Suitable organic peroxides, especially diacyl peroxides, are further illustrated in "Initiators for Polymer Production", Akzo Chemicals Inc., Product Catalog, Bulletin No. 88-57, incorporated by reference. Preferred diacyl peroxides herein whether in pure or formulated form for granule, powder or tablet forms of the bleaching compositions constitute solids at 25° C., e.g., CADET® BPO 78 powder form of dibenzoyl peroxide, from Akzo. Highly preferred organic peroxides, particularly the diacyl peroxides, for such bleaching compositions have melting points above 40° C., preferably above 50° C. Additionally, preferred are the organic peroxides with SADT's (as defined in the foregoing Akzo publication) of 35° C. or higher, more preferably 70° C. or higher. Nonlimiting examples of diacyl peroxides useful herein include dibenzoyl peroxide, lauroyl peroxide, and dicumyl peroxide. Dibenzoyl peroxide is preferred. In some instances, diacyl peroxides are available in the trade which contain oily substances such as dioctyl phthalate. In general, particularly for automatic dishwashing applications, it is preferred to use diacyl peroxides which are substantially free from oily phthalates since these can form smears on dishes and glassware.

Conventional Quaternary Substituted Bleach Activators—The present compositions can optionally further comprise conventional, known quaternary substituted bleach activators (CQSBA). CQSBA's are further illustrated in U.S. Pat. No. 4,539,130, Sept. 3, 1985 and U.S. Pat. No. 4,283,301. British Pat. 1,382,594, published Feb. 5, 1975, discloses a class of CQSBA's optionally suitable for use herein. U.S. Pat. No. 4,818,426 issued Apr. 4., 1989 discloses another class of CQSBA's. Also see U.S. Pat. No. 5,093,022 issued Mar. 3, 1992 and U.S. Pat. No. 4,904,406, issued Feb. 27, 1990. Additionally, CQSBA's are described in EP 552,812 A1 published Jul. 28, 1993, and in EP 540,090 A2, published May 5, 1993. Particularly preferred are CQSBA's having a caprolactam or valerolactam leaving group, and are the subject of copending applications, in particular co-pending commonly assigned British Patent Appl. Ser. No. 9407944.9, filed Apr. 21, 1994, P&G Case No. CM705F.

Detersive Surfactants—Nonlimiting examples of surfactants useful herein include the conventional $C_{11}$–$C_{18}$ alkylbenzene sulfonates "LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3\text{-}M^+)CH_3$ and $CH_3(CH_2)_y(CHOSO_3\text{-}M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1-7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxylate/propoxylates), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Automatic dishwashing compositions typically employ low sudsing surfactants, such as the mixed ethyleneoxy/propyleneoxy nonionics. Other conventional useful surfactants are listed in standard texts.

Builders— Detergent builders can optionally be included in the compositions herein to assist in controlling mineral hardness. Inorganic as well as organic builders can be used. Builders are typically used in automatic dishwashing and fabric laundering compositions to assist in the removal of particulate soils.

The level of builder can vary widely depending upon the end use of the composition and its desired physical form. When present, the compositions will typically comprise at least about 1% builder. High performance compositions typically comprise from about 10% to about 80%, more typically from about 15% to about 50% by weight, of the detergent builder. Lower or higher levels of builder, however, are not excluded.

Inorganic or P-containing detergent builders include, but are not limited to, the alkali metal, ammonium and alkanolammonium salts of polyphosphates (exemplified by the tripolyphosphates, pyrophosphates, and glassy polymeric metaphosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphated) such as citrate, or in the so-called "underbuilt" situation that may occur with zeolite or layered silicate builders. For examples of preferred aluminosilicates see U.S. Pat. No. 4,605,509.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6® is a crystalline layered silicate marketed by Hoechst (commonly abbreviated herein as "SKS-6"). Unlike zeolite builders, the Na SKS-6 silicate builder does not contain aluminum. NaSKS-6 is the δ-$Na_2SiO_5$ morphology form of layered silicate and can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1}.yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the α-, β- and γ-forms. Other silicates may also be useful, such as for example magnesium silicate, which can serve as a crispening agent o in granular formulations, as a stabilizing agent for oxygen bleaches, and as a component of suds control systems.

Silicates useful in automatic dishwashing (ADD) applications include granular hydrous 2-ratio silicates such as BRITESIL® H20 from PQ Corp., and the commonly sourced BRITESIL® H24 though liquid grades of various silicates can be used when the ADD composition has liquid form. Within safe limits, sodium metasilicate or sodium hydroxide alone or in combination with other silicates may be used in an ADD context to boost wash pH to a desired level.

Examples of carbonate builders are the alkaline earth and alkali metal carbonates as disclosed in German Patent Application No. 2,321,001 published on Nov. 15, 1973. Various grades and types of sodium carbonate and sodium sesquicarbonate may be used, certain of which are particularly useful as carriers for other ingredients, especially detersive surfactants.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula: $[M_z(zAlO_2)_y].xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula: $Na_{12}[(AlO_2)_{12}(SiO_2)_{12}].xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter. As with other builders such as carbonates, it may be desirable to use zeolites in any physical or morphological form adapted to promote surfactant carrier function, and appropriate particle sizes may be freely selected by the formulator.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt or "overbased". When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lambeni et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediaminetetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty laundry detergent formulations due to their availability from renewable resources and their biodegradability. Citrates can also be used in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1 -hydroxy-1,1-diphosphonate and other known phosphonates (see, for example, U.S. Pat. Nos. 3,159,581; 3,213,030; 3,422,021; 3,400,148 and 3,422,137) can also be used.

Chelating Agents—The compositions herein may also optionally contain one or more iron and/or manganese chelating agents, such as hydroxyethyldiphosphonate (HEDP). More generally, chelating agents suitable for use herein can be selected from the group consisting of aminocarboxylates, aminophosphonates, polyfunctionally-substituted aromatic chelating agents and mixtures thereof. Without intending to be bound by theory, it is believed that the benefit of these materials is due in part to their exceptional ability to remove iron and manganese ions from washing solutions by formation of soluble chelates; other benefits include inorganic film or scale prevention. Other suitable chelating agents for use herein are the commercial DEQUEST® series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts therein and mixtures therein.

Aminophosphonates are also suitable for use as chelating agents in the compositions of the invention when at least low levels of total phosphorus are permitted in detergent compositions, and include ethylenediaminetetrakis (methylenephosphonates). Preferably, these aminophosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A highly preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred though other forms, such as Magnesium salts, may also be useful.

If utilized, especially in ADD compositions, these chelating agents or transition-metal-selective sequestrants will preferably comprise from about 0.001% to about 10%, more preferably from about 0.05% to about 1% by weight of the bleaching compositions herein.

Enzymes— Enzymes can be included in the formulations herein for a wide variety of fabric laundering or other cleaning purposes, including removal of protein-based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders, etc. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of *B. subtilis* and *B. licheniformis*. Another suitable protease is obtained from a strain of Bacillus, having maximum activity throughout the pH range of 8–12, developed and sold by Novo Industries A/S as ESPERASE®. The preparation of this enzyme and analogous enzymes is described in British Patent Specification No. 1,243,784 of Novo. Proteolytic enzymes suitable for removing protein-based stains that are commercially available include those sold under the tradenames ALCALASE® and SAVINASE® by Novo Industries A/S (Denmark) and MAXATASE® by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bon et al, published Jan. 9, 1985).

An especially preferred protease, referred to as "Protease D" is a carbonyl hydrolase variant having an amino acid sequence not found in nature, which is derived from a precursor carbonyl hydrolasc by substituting a different amino acid for a plurality of amino acid residues at a position in said carbonyl hydrolasc equivalent to position +76 in combination with one or more amino acid residue positions equivalent to those selected from the group consisting of +99, +101, + 103, +107 and +123 in *Bacillus amyloliquefaciens* subtilisin as described in the patent applications of A. Baeck, C. K. Ghosh, P. P. Greycar, R. R. Bott and L. J. Wilson, entitled "Protease-Containing Cleaning Compositions" having U.S. Ser. No. 08/136,797 (P&G Case 5040), and "Bleaching Compositions Comprising Protease Enzymes" having U.S. Ser. No. 08/136,626.

Amylases include, for example, ct-amylases described in British Patent Specification No. 1,296,839 (Novo), RAPIDASE®, International Bio-Synthetics, Inc. and TERMAMYL®, Novo Industries.

Cellulases usable in the present invention include both bacterial or fungal cellulases. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from *Humicola insolens* and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS-2.247.832. CAREZYME® (Novo) is especially useful.

Suitable lipase enzymes for detergent use include those produced by microorganisms of the Pseudomonas group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. lipolyticum NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*. The LIPOLASE® enzyme derived from *Humicola lanuginosa* and commercially available from Novo (see also EPO 341,947) is a preferred lipase for use herein.

Peroxidase enzymes can be used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/0998 13, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

Other Ingredients—Usual detersive ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. Adjuncts which can also be included in detergent compositions employed in the present invention, in their conventional art-established levels for use (generally from 0% to about 20% of the detergent ingredients, preferably from about 0.5% to about 10%), include other active ingredients such as dispersant polymers from BASF Corp. or Rohm & Haas; color speckles, anti-tarnish and/or anti-corrosion agents, dyes, fillers, optical brighteners, germicides, alkalinity sources, hydrotropes, anti-oxidants, enzyme stabilizing agents, perfumes, solubilizing agents, clay soil removal/anti-redeposition agents, carriers, processing aids, pigments, solvents for liquid formulations, fabric softeners, static control agents, solid fillers for bar compositions, etc. Dye transfer inhibiting agents, including polyamine N-oxides such as polyvinylpyridine N-oxide can be used. Dye-transfer-inhibiting agents are further illustrated by polyvinylpyrrolidone and copolymers of N-vinyl imidazole and N-vinyl pyrrolidone. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate With a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT® D10, Degussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid or gel compositions can contain some water and other fluids as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

Certain bleaching compositions herein among the generally encompassed liquid (easily flowable or gel forms) and solid (powder, granule or tablet) forms, especially bleach additive compositions and hard surface cleaning compositions, may preferably be formulated such that the pH is acidic during storage and alkaline during use in aqueous cleaning operations, i.e., the wash water will have a pH in the range from about 7 to about 11.5. Laundry and automatic dishwashing products are typically at pH 7–12, preferably 9 to 11.5. Automatic dishwashing compositions, other than rinse aids which may be acidic, will typically have an aqueous solution pH greater than 7. Techniques for controlling pH at recommended usage levels include the use of buffers, alkalis, acids, pH-jump systems, dual compartment containers, etc., and are well known to those skilled in the art. The compositions are useful from about 5° C. to the boil for a variety of cleaning and bleaching operations.

Bleaching compositions in granular form typically limit water content, for example to less than about 7% free water, for best storage stability.

Storage stability of bleach compositions can be further enhanced by limiting the content in the compositions of adventitious redox-active substances such as rust and other traces of transition metals in undesirable form. Certain bleaching compositions may moreover be limited in their total halide ion content, or may have any particular halide, e.g., bromide, substantially absent. Bleach stabilizers such as stannates can be added for improved stability and liquid formulations may be substantially nonaqueous if desired.

The following examples illustrate the perhydrolysis-selective bleach activators of the invention, intermediates for making same and bleaching compositions which can be prepared using the activators, but are not intended to be limiting thereof.

EXAMPLE I

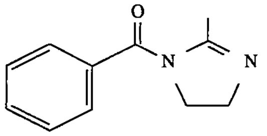

1-Benzoyl-4,5-dihydro-2-methyl-1H-imidazole—A single neck, 500 mL round bottom flask equipped with magnetic stirring, a pressure equalizing addition funnel and an argon line is charged with 60 mL toluene, 10.0 g (119 mmol) 4,5 -dihydro-2-methyl-1H-imidazole and 13.1 g (130 mmol, 1.1 equiv)triethylamine. The mixture is heated to 80° C. and a solution of 15.2 g (108 mmol, 1.0 equiv) benzoyl chloride in 40 mL toluene is added over a period of about 40 minutes. The addition funnel is replaced with a reflux condenser, heated to reflux overnight, cooled to room temperature and filtered to remove solids. The filtrate is condensed under reduced pressure and purified by flash chromatography on silica gel using gradient elution (0–2% methanol in dichloromethane) to yield 18.3 g (90%) of an oil that solidifies slowly to a solid on standing.

EXAMPLE II

The synthesis of Example I is repeated but with substitution of octanoyl chloride for benzoyl chloride.

EXAMPLE III

The synthesis of Example I is repeated but with substitution of nonanoyl chloride for benzoyl chloride.

EXAMPLE IV

The synthesis of Example I is repeated but with substitution of decanoyl chloride for benzoyl chloride.

EXAMPLE Va

The synthesis of Example I is repeated but with substitution of 4-nitrobenzoyl chloride for benzoyl chloride.

EXAMPLE Vb

The synthesis of Example I is repeated but with substitution of 3-chlorobenzoyl chloride for benzoyl chloride.

EXAMPLE Vc

The synthesis of Example I is repeated but with substitution of 4-tertbutylbenzoyl chloride for benzoyl chloride.

EXAMPLE Vd

The synthesis of Example I is repeated but with substitution of isononanoyl chloride for benzoyl chloride.

EXAMPLE Ve

The synthesis of Example I is repeated but with substitution of 2-ethylhexanoyl chloride for benzoyl chloride.

EXAMPLE Vf

The synthesis of Example I is repeated but with substitution of 6-(nonanamido)caproyl chloride for benzoyl chloride.

EXAMPLE Vg

The synthesis of Example I is repeated but with substitution of one half equivalent of terephthaloyl chloride for benzoyl chloride.

EXAMPLE Vh

The synthesis of Example I is repeated but with substitution of nonylaminoadipoyl chloride for benzoyl chloride.

EXAMPLE VI

Granular laundry detergents are exemplified by the following formulations.

| EXAMPLE VI | A | B | C | D | E |
|---|---|---|---|---|---|
| INGREDIENT | % | % | % | % | % |
| PSBA* | 5 | 5 | 3 | 3 | 8 |
| Sodium Percarbonate | 0 | 0 | 19 | 21 | 0 |
| Sodium Perborate monohydrate | 21 | 0 | 0 | 0 | 20 |
| Sodium Perborate tetrahydrate | 12 | 21 | 0 | 0 | 0 |
| Tetraacetylethylenediamine | 0 | 0 | 0 | 3 | 0 |
| Nonanoyloxybenzenesulfonate | 0 | 0 | 3 | 0 | 0 |
| Linear alkylbenzenesulfonate | 7 | 11 | 19 | 12 | 8 |
| Alkyl ethoxylate (C45E7) | 4 | 0 | 3 | 4 | 6 |
| Zeolite A | 20 | 20 | 7 | 17 | 21 |
| SKS-6 ® silicate (Hoechst) | 0 | 0 | 11 | 11 | 0 |
| Trisodium citrate | 5 | 5 | 2 | 3 | 3 |
| Acrylic Acid/Maleic Acid copolymer | 4 | 0 | 4 | 5 | 0 |
| Sodium polyacrylate | 0 | 3 | 0 | 0 | 3 |
| Diethylenetriamine penta(methylene phosphonic acid) | 0.4 | 0 | 0.4 | 0 | 0 |
| DTPA | 0 | 0.4 | 0 | 0 | 0.4 |
| EDDS | 0 | 0 | 0 | 0.3 | 0 |
| Carboxymethylcellulose | 0.3 | 0 | 0 | 0.4 | 0 |
| Protease | 1.4 | 0.3 | 1.5 | 2.4 | 0.3 |
| Lipolase | 0.4 | 0 | 0 | 0.2 | 0 |
| Carezyme | 0.1 | 0 | 0 | 0.2 | 0 |
| Anionic soil release polymer | 0.3 | 0 | 0 | 0.4 | 0.5 |
| Dye transfer inhibiting polymer | 0 | 0 | 0.3 | 0.2 | 0 |
| Sodium Carbonate | 16 | 14 | 24 | 6 | 23 |
| Sodium Silicate | 3.0 | 0.6 | 12.5 | 0 | 0.6 |
| Sulfate, Water, Perfume, Colorants | to 100 | to 100 | to 100 | to 100 | to 100 |

*Perhydrolysis-Selective Bleach Activator of any of Examples I to V

Additional granular laundry detergents are exemplified by the following

| EXAMPLE VI | F | G | H | I |
|---|---|---|---|---|
| INGREDIENT | % | % | % | % |
| PSBA* | 5 | 3 | 6 | 4.5 |
| Sodium Percarbonate | 20 | 21 | 21 | 21 |
| Tetraacetylethylenediamine | 0 | 6 | 0 | 0 |
| Nonanoyloxybenzenesulfonate | 4.5 | 0 | 0 | 4.5 |
| Alkyl ethoxylate (C45E7) | 2 | 5 | 5 | 5 |
| N-cocoyl N-methyl glucamine | 0 | 4 | 5 | 5 |
| Zeolite A | 6 | 5 | 7 | 7 |
| SKS-6 ® silicate (Hoechst) | 12 | 7 | 10 | 10 |
| Trisodium citrate | 8 | 5 | 3 | 3 |
| Acrylic Acid/Maleic Acid copolymer | 7 | 5 | 7 | 8 |

-continued

| EXAMPLE VI | F | G | H | I |
|---|---|---|---|---|
| Diethylenetriamine penta-(methylene phosphonic acid) | 0.4 | 0 | 0 | 0 |
| EDDS | 0 | 0.3 | 0.5 | 0.5 |
| Carboxymethylcellulose | 0 | 0.4 | 0 | 0 |
| Protease | 1.1 | 2.4 | 0.3 | 1.1 |
| Lipolase | 0 | 0.2 | 0 | 0 |
| Carezyme | 0 | 0.2 | 0 | 0 |
| Anionic soil release polymer | 0.5 | 0.4 | 0.5 | 0.5 |
| Dye transfer inhibiting polymer | 0.3 | 0.02 | 0 | 0.3 |
| Sodium Carbonate | 21 | 10 | 13 | 14 |
| Sulfate, Water, Perfume, Colorants | to 100 | to 100 | to 100 | to 100 |

*Perhydrolysis-Selective Bleach Activator of any of Examples I to V

EXAMPLE VII

A simple, effective fabric bleach designed to be dissolved in water prior to use is as follows:

| Ingredient | % (wt.) |
|---|---|
| MSBA* | 7.0 |
| Sodium Perborate (monohydrate) | 50.0 |
| Chelant (EDDS) | 10.0 |
| Sodium Silicate | 5.0 |
| Sodium Sulfate | Balance |

*Bleach Activator of any of Examples I–V.

In an alternate embodiment, the composition is modified by replacing the sodium perborate with sodium percarbonate.

EXAMPLE VIII

A simple, yet effective, fabric bleach designed to be dissolved in water prior to use is as follows:

| Ingredient | % (wt.) |
|---|---|
| PSBA* | 7.0 |
| Sodium Perborate (monohydrate) | 50.0 |
| $C_{12}$ Alkyl Sulfate, Na | 4.5 |
| Citric acid | 6.0 |
| $C_{12}$ Pyrrolidone | 0.6 |
| Chelant (DTPA) | 0.5 |
| Perfume | 0.4 |
| Filler and water | Balance to 100% |

*Perhydrolysis-Selective Bleach Activator of any of Examples I–V.

The composition is prepared by admixing the indicated ingredients. In an alternate embodiment, the composition is modified by replacing the sodium perborate with sodium percarbonate.

EXAMPLE IX

A simple, yet effective, fabric bleach designed to be dissolved in water prior to use is as follows:

| Ingredient | % (wt.) |
|---|---|
| PSBA* | 7.0 |
| Sodium Perborate (monohydrate) | 30.0 |
| Zeolite A | 20.0 |
| Chelant | 3.0 |
| $C_{12}$ Alkyl Sulfate, Na | 4.5 |
| Citric Acid | 6.0 |
| $C_{12}$ Pyrrolidone | 0.7 |
| Perfume | 0.4 |
| Filler and water | Balance to 100% |

*Perhydrolysis-Selective Bleach Activator of any of Examples I–V.

The composition is prepared by admixing the indicated ingredients. In an alternate embodiment, the composition is modified by replacing the sodium perborate with sodium percarbonate. In an alternate embodiment, the composition is modified by replacing the Zeoltie A with Zeolite P.

EXAMPLE X

An abrasive thickened liquid composition especially useful for cleaning bathtubs and shower tiles is formed upon addition of the following composition to water.

| Ingredient | % (wt.) |
|---|---|
| PSBA* | 7.0 |
| Sodium Perborate (monohydrate) | 50.0 |
| $C_{12}$ AS, Na | 5.0 |
| $C_{12-14}$ $AE_3S$, Na | 1.5 |
| $C_8$ Pyrrolidone | 0.8 |
| Oxydisuccinic Acid | 0.5 |
| Sodium citrate | 5.5 |
| Calcium carbonate abrasive (15–25 micrometer) | 15.0 |
| Filler and water | Balance to 100% |
| Product pH upon dilution | Adjust to 10 |

*Perhydrolysis-Selective Bleach Activator of any of Examples I–V.

EXAMPLE XI

A bleaching composition which provides benefits with respect to the removal of soil from shower walls and bathtubs, is formed upon combining the following: in water:

| Ingredient | % (wt.) |
|---|---|
| PSBA* | 7.0 |
| Sodium Perborate (monohydrate) | 50.0 |
| $C_{12}$ AS, Na | 5.0 |
| $C_8E_4$ Nonionic | 1.0 |
| Sodium citrate | 6.0 |
| $C_{12}$ Pyrrolidone | 0.75 |
| Perfume | 0.6 |
| Filler and water | Balance to 100% |

*Perhydrolysis-Selective Bleach Activator of any of Examples I–V.

EXAMPLE XII

Granular automatic dishwashing detergent composition comprise the following.

| Example XII | A | B | C | D |
|---|---|---|---|---|
| INGREDIENT | wt % | wt % | wt % | wt % |
| PSBA (See Note 1) | 3 | 4.5 | 2.5 | 4.5 |
| Sodium Perborate Monohydrate (See Note 2) | 1.5 | 0 | 1.5 | 0 |
| Sodium Percarbonate (See Note 2) | 0 | 1.2 | 0 | 1.2 |
| Amylase (TERMAMYL ® from NOVO) | 2 | 2 | 2 | 2 |
| Dibenzoyl Peroxide | 0 | 0 | 0.8 | 0 |
| Transition Metal Bleach Cata- | 0.1 | 0.1 | 0.1 | 0 |

-continued

| Example XII | A | B | C | D |
|---|---|---|---|---|
| lyst (See Note 3) | | | | |
| Conventional Bleach Activator (TAED or NOBS) | 1 | 0 | 3 | 0 |
| Protease (SAVINASE ® 12 T, NOVO, 3.6% active protein) | 2.5 | 2.5 | 2.5 | 2.5 |
| Trisodium Citrate Dehydrate (anhydrous basis) | 15 | 15 | 15 | 15 |
| Sodium Carbonate, anhydrous | 20 | 20 | 20 | 20 |
| BRITESIL H2O ®, PQ Corp. (as $SiO_2$) | 10 | 8 | 7 | 5 |
| Diethylenetriaminepenta-(methylenephosphonic acid), Na | 0 | 0 | 0 | 0.2 |
| Hydroxyethyldiphosphonate (HEDP), Sodium Salt | 0 | 0.5 | 0 | 0.5 |
| Ethylenediaminedisuccinate, Trisodium Salt | 0.1 | 0.3 | 0 | 0 |
| Dispersant Polymer (Accusol ® 480N) | 8 | 5 | 8 | 10 |
| Nonionic Surfactant (LF404, BASF) | 1.5 | 1.5 | 1.5 | 1.5 |
| Paraffin (Winog 70 ®) | 1 | 1 | 1 | 0 |
| Benzotriazole | 0.1 | 0.1 | 0.1 | 0 |
| Sodium Sulfate, water, minors BALANCE TO: | 100% | 100% | 100% | 100% |

Note 1: Bleach Activator of Example 1. This PSBA may be substituted by use of a PSBA according to any of Examples II-V;
Note 2: These hydrogen peroxide sources are expressed on a weight % available oxygen basis. To convert to a basis of percentage of the total composition, divide by about 0.15;
Note 3: Transition Metal Bleach Catalyst: MnEDDS according to U.S. Application Ser. No. 08/210,186, filed March 17, 1994.

EXAMPLE XIII

This Example illustrates liquid bleach compositions in accordance with the invention, all made by the general process described hereinafter. The desired amount of a chelating agent is added to a beaker of water, after which the resulting solution is stirred until the chelating agent is completely dissolved. A phase stabilizer is added to the solution while it is being continuously stirred. Thereafter, the bleach activator and optionally an additional chelating agent is added to the solution. The pH of the solution is adjusted to about 4.0 with an alkaline adjusting agent such as sodium hydroxide.

The following translucent, stable aqueous liquid bleach compositions (Samples A–F) are made as described above, all amounts being expressed as percentages by weight.

| Example XIII | A | B | C | D | E | F | G |
|---|---|---|---|---|---|---|---|
| Ingredients | wt % | wt % | wt % | wt % | wt % | wt % | wt % |
| Water | 76 | 81 | 84 | 70 | 73 | 75 | 71 |
| NEODOL 91-10[1] | 10 | 10 | 10 | 10 | 10 | 10 | 10 |
| NEODOL 23-2[1] | — | — | — | 5 | 5 | 5 | 5 |
| DEQUEST 2010[2] | 0.5 | 0.1 | 0.1 | 1.0 | 0.5 | 0.5 | 1.0 |
| PSBA[3] | 6 | 6 | 4 | 7 | 4 | 4 | 8 |
| Citric Acid | 0.5 | 0.5 | 0.5 | 0.5 | 0.5 | 0.5 | 0.5 |
| NaOH | to pH 4 | to pH 4 | to pH 4 | to pH 4 | to pH 4 | to pH 4 | to pH 4 |
| Hydrogen Peroxide | 7 | 3 | 2 | 7 | 7 | 5 | 5 |

[1]Alkyl ethoxylate available from The Shell Oil Company.
[2]Hydroxy-ethylidene diphosphonic acid commercially available from Monsanto Co.
[3]Perhydrolysis-Selective Bleach activator according to any of Examples I–V.

EXAMPLE XIV

A laundry bar suitable for hand-washing soiled fabrics is prepared comprising the following ingredients.

| Component | Weight % |
|---|---|
| $C_{12}$ linear alkyl benzene sulfonate | 30 |
| Phosphate (as sodium tripoly-phosphate) | 7 |
| Sodium carbonate | 15 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| PSBA** | 6.5 |
| Sodium percarbonate | 15 |
| Brightener, perfume | 0.2 |
| Protease | 0.3 |
| $CaSO_4$ | 1 |
| $MgSO_4$ | 1 |
| Water and Filler* | Balance to 100% |

*Selected from convenient materials e.g., $CaCO_3$, talc, clay, silicates, and the like.
**Perhydrolysis-Selective Bleach activator according to any of Examples I-V.

The detergent laundry bar is extruded in conventional soap or detergent bar making equipment as commonly used in the art.

EXAMPLE XV

A laundry bar suitable for hand-washing soiled fabrics is prepared comprising the following ingredients.

| Component | Weight % |
|---|---|
| Linear alkyl benzene sulfonate | 30 |
| Phosphate (as sodium tripoly-phosphate) | 7 |
| Sodium carbonate | 20 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| PSBA** | 5 |
| Sodium perborate tetrahydrate | 10 |
| Brightener, perfume | 0.2 |
| Protease | 0.3 |

-continued

| Component | Weight % |
|---|---|
| $CaSO_4$ | 1 |

-continued

| Component | Weight % |
|---|---|
| $MgSO_4$ | 1 |
| Water | 4 |
| Filler* | Balance to 100% |

*Selected from convenient materials e.g., $CaCO_3$, talc, clay, silicates, and the like.
**Perhydrolysis-Selective Bleach activator according to any of Examples I–V.

A detergent laundry bar is formed using conventional soap or detergent bar making equipment as commonly used in the art with the bleaching activator dry-mixed with the perborate bleaching compound and not affixed to the surface of the perborate.

EXAMPLE XVI

Liquid bleaching compositions for cleaning typical househould surfaces are as follows. The hydrogen peroxide is separated as an aqueous solution from the other components by suitable means, such as a dual-chamber container.

| Component | A wt % | B wt % |
|---|---|---|
| $C_{8-10}$ $E_6$ nonionic surfactant | 20 | 15 |
| $C_{12-13}$ $E_3$ nonionic surfactant | 4 | 4 |
| $C_8$ alkyl sulfate anionic surfactant | 0 | 7 |
| $Na_2CO_3/NaHCO_3$ | 1 | 2 |
| $C_{12-18}$ Fatty Acid | 0.6 | 0.4 |
| Hydrogen peroxide | 7 | 7 |
| PSBA** | 7 | 7 |
| DEQUEST 2010* | 0.05 | 0.05 |
| $H_2O$ | Balance to 100 | Balance to 100 |

*Hydroxy-ethylidene diphosphonic acid, Monsanto Co.
**Perhydrolysis-Selective Bleach activator according to any of Examples I–V.

What is claimed is:

1. A bleach activator having the formula:

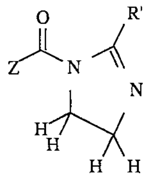

wherein Z is selected from the group consisting of $C_2$–$C_{16}$ linear or branched, substituted or unsubstituted alkyl, alkaryl, aralkyl and aryl, and mixtures thereof; and R' is selected from the group consisting of H, ethoxylated alkyl, carboxylated alkyl, sulfated alkyl, sulfonated alkyl, phenyl, and mixtures thereof.

2. A bleach activator according to claim 1 wherein Z is selected from the group consisting of phenyl, nitrophenyl, chlorophenyl, t-butylphenyl, and $C_8$–$C_{12}$ linear or branched alkyl; and wherein R' is H or methyl.

3. A bleach activator according to claim 1 wherein R' is selected from the group consisting of carboxylated alkyl, sulfated alkyl and sulfonated alkyl, and wherein the anionic charge of said R' is balanced by a cation selected from the group consisting of $H^+$, $Na^+$, $K^+$, and $C_1$–$C_4$ quaternary ammonium.

4. A bleach activator having the formula:

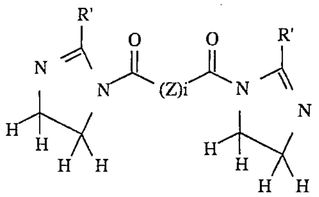

wherein i is 0 or 1 and z is selected from the group consisting of $C_2$–$C_{16}$ linear or branched, substituted or unsubstituted alkyl, alkaryl, aralkyl and aryl, and mixtures thereof, and R' is selected from the group consisting of H, $C_1$–$C_5$ alkyl, ethoxylated alkyl, carboxylated alkyl, sulfated alkyl, sulfonated alkyl, phenyl, substituted phenyl, and mixtures thereof.

5. A bleach activator according to claim 4 wherein Z is p-$C_6H_4$.

* * * * *